(12) United States Patent
Mariella, Jr.

(10) Patent No.: US 7,452,666 B2
(45) Date of Patent: Nov. 18, 2008

(54) SYNTHESIS OF DNA

(75) Inventor: Raymond P. Mariella, Jr., Danville, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 946 days.

(21) Appl. No.: 10/394,911

(22) Filed: Mar. 21, 2003

(65) Prior Publication Data

US 2003/0180782 A1 Sep. 25, 2003

Related U.S. Application Data

(60) Provisional application No. 60/367,989, filed on Mar. 25, 2002.

(51) Int. Cl.
*C12Q 1/68* (2006.01)
*C07H 21/04* (2006.01)

(52) U.S. Cl. .......................... 435/6; 536/23.1

(58) Field of Classification Search ............ 435/6, 435/91.2; 536/23.1, 24.31, 24.32
See application file for complete search history.

(56) References Cited

U.S. PATENT DOCUMENTS

| | | | |
|---|---|---|---|
| 6,375,903 B1 | 4/2002 | Cerrina et al. | |
| 6,444,468 B1 | 9/2002 | Stemmer et al. | |
| 6,824,664 B1 * | 11/2004 | Austin et al. | 204/643 |
| 2002/0042069 A1 | 4/2002 | Myer et al. | |
| 2002/0160366 A1 | 10/2002 | Dupret et al. | |
| 2002/0183934 A1 | 12/2002 | Selifonov et al. | |

FOREIGN PATENT DOCUMENTS

| | | |
|---|---|---|
| WO | WO 9914318 A1 * | 3/1999 |
| WO | WO 99/42813 A1 | 8/1999 |
| WO | WO 02/04597 A2 | 1/2002 |
| WO | WO 02/095073 A1 | 11/2002 |

OTHER PUBLICATIONS

Stemmer et al. Single-step assembly of a gene and entire plasmid from large numbers of oligodeoxyribonucleotides. Gene, vol. 164, p. 49-53, 1995.*

Heller et al. Active microelectronic chip devices which utilize controlled electrophoretic fields for multiplex DNA hybridization and other genomic applications. Electrophoresis, vol. 21, pp. 157-164, 2000.*

Stemmer, W., et al., "Single-step assembly of a gene and entire plasmid from large numbers of oligodeoxyribonucleotides," Elsevier Science B.V., Gene, 164 (1995) pp. 49-53.

Heller, M. J., et al., "Active microelectronic chip devices which utilize controlled electrophoretic fields for multiplex DNA hybridization and other genomic applications," Electrophoresis 2000, 21, Wiley-VCH Verlat GmbH, 69451 Weinheim, (2000) pp. 157-164.

* cited by examiner

*Primary Examiner*—Suryaprabha Chunduru
(74) *Attorney, Agent, or Firm*—Eddie E. Scott; John H. Lee

(57) ABSTRACT

A method of synthesizing a desired double-stranded DNA of a predetermined length and of a predetermined sequence. Preselected sequence segments that will complete the desired double-stranded DNA are determined. Preselected segment sequences of DNA that will be used to complete the desired double-stranded DNA are provided. The preselected segment sequences of DNA are assembled to produce the desired double-stranded DNA.

21 Claims, 3 Drawing Sheets

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Synthetic Construct

<400> SEQUENCE: 1
gacctgcgca at                                                          12

<210> SEQ ID NO 2
<211> LENGTH: 12
```

-continued

```
<212> TYPE: DNA
<213> ORGANISM: Artificial Sequence
<220> FEATURE:
<223> OTHER INFORMATION: Synthetic Construct

<400> SEQUENCE: 2
attgcgcagg tc                                                          12
```

SYNTHESIS OF DNA

CROSS-REFERENCE TO RELATED APPLICATIONS

This application claims the benefit of U.S. Provisional Application No. 60/367,989 filed Mar. 25, 2002 titled "Synthesis of DNA via Array-Based Ligation." U.S. Provisional Application No. 60/367,989 filed Mar. 25, 2002 titled "Synthesis of DNA via Array-Based Ligation" is incorporated in this application by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to DNA sequences and more particularly to synthesizing DNA sequences.

2. State of Technology

U.S. Pat. No. 6,375,903 issued Apr. 23, 2002 to Francesco Cerrina et al. for a method and apparatus for synthesis of arrays of DNA probes provides the following background information, "The sequencing of deoxyribonucleic acid (DNA) is a fundamental tool of modern biology and is conventionally carried out in various ways, commonly by processes which separate DNA segments by electrophoresis . . . One such alternative approach, utilizing an array of oligonucleotide probes synthesized by photolithographic techniques is described in Pease, et al., "Light-Generated Oligonucleotide Arrays for Rapid DNA Sequence Analysis," Proc. Natl. Acad. Sci. USA, Vol. 91, pp. 5022-5026, May 1994."

International Patent Application WO 02/095073 by Peter J. Belshaw, Michael, R. Sussman, and Francesco Cerrina published Nov. 28, 2002 and assigned to the Wisconsin Alumni Research Foundation describes a method for constructing a DNA construct of defined sequence. The method begins with breaking up the sequence into a plurality of overlapping DNA segments using computer software. A DNA microarray is then made on a substrate in such a way that each single stranded probe on the array is constructed to be one of the overlapping DNA segments needed to make up the desired DNA construct. Then the probes are all released from the substrate. The probes will then self assemble into the desired DNA construct.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a method of synthesizing a desired double-stranded DNA of a predetermined length and of a predetermined sequence. Preselected sequence segments that will complete the desired double-stranded DNA are determined. Preselected segment sequences of DNA that will be used to complete the desired double-stranded DNA are provided. The preselected segment sequences of DNA are assembled to produce the desired double-stranded DNA. In one embodiment the determination of the preselected sequence segments that will complete the desired double-stranded DNA is a result of analyzing the desired double-stranded DNA by a computer program.

In another embodiment the assembling the preselected segment sequences of DNA to produce the desired double-stranded DNA comprises multiple substeps of assembling individual preselected segment sequences of DNA that complete the desired double-stranded DNA to produce the desired double-stranded DNA. In another embodiment at least some of the multiple substeps are performed in parallel. In another embodiment at least some of the multiple substeps are performed in sequence. In another embodiment at least some of the multiple substeps are performed using non-consumable, tethered templates in a parallel process. In another embodiment at least some of the multiple substeps are performed by ligating the individual preselected segment sequences of DNA that complete the desired double-stranded DNA to produce the desired double-stranded DNA. In another embodiment at least some of the multiple substeps are performed using non-consumable, tethered templates in a parallel process. In another embodiment at least some of the multiple substeps themselves comprise assembling subsets of individual preselected segment sequences of DNA and assembling the subsets of preselected segment sequences of DNA to produce the preselected segment sequences of DNA.

In another embodiment the step of assembling the preselected segment sequences of DNA to produce the desired double-stranded DNA comprises preselecting an initial segment of DNA of the desired length and predetermined sequence, tethering the initial segment of DNA of the desired length and predetermined sequence, preselecting a multiplicity of DNA sequence segments that will comprise the DNA of a desired length and of a predetermined sequence, applying a voltage to the initial segment of DNA of the desired length and predetermined sequence for hybridization of the multiplicity of DNA sequence segments, and ligating the multiplicity of DNA sequence segments to produce the DNA of a desired length and of a predetermined sequence.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
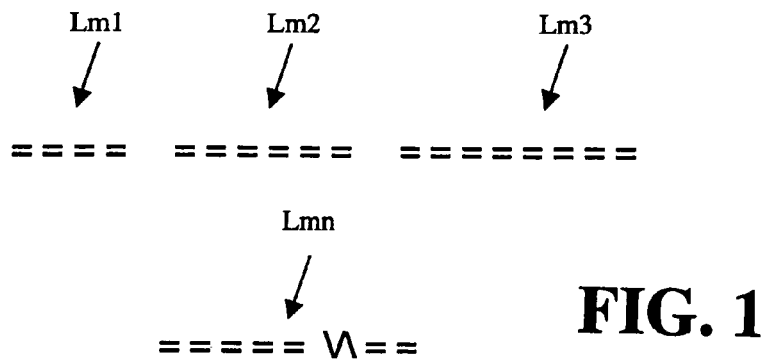
FIG. 1 illustrates a system for synthesizing double-stranded, ds-DNA, of a desired length, "L," and of a predetermined sequence, using parallel syntheses of shorter segments of ds-DNA that are later assembled into the desired full-length sequence.

Artificial gene synthesis is a widely used tool in molecular biology. Uses include such common biological purposes as genes for transgenic studies, genetic engineering and mutagenesis, and uses as esoteric as encryption and DNA computing. A casual survey of gene synthesis service websites provides a cost per base of approximately $10.00 for genes longer than 2 kilobases; as the average gene is around 7000 bases, it is reasonable to expect to pay in the neighborhood of $70,000 to purchase an artificial gene. It is this cost, and the considerable delivery time, that has kept artificial genes from being as widely-used as they might otherwise be. DNA computing, for example, requires much more rapid turnaround; hours or days rather than weeks or months are necessary.

There is the need for thousands or tens of thousands of oligomers (4 to 20 bases in length, for example) that must be joined together (ligated) to form the much longer strand of DNA. The utility of synthetic long DNA and artificial genes is limited by the cost and time required to produce them. The cost factors involved are labor, the oligonucleotides that serve as building blocks for the final product, enzymes and sequencing verification.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIG. 1, one embodiment of the present invention provides a system for synthesizing double-stranded, ds-DNA, of a desired length, "L," and of a predetermined sequence, using parallel syntheses of shorter segments of ds-DNA that are later assembled into the desired full-length sequence. To begin, a multiplicity of shorter ds-DNA sequence segments, of lengths Lm1, Lm2, Lm3, through Lmn, and of predetermined sequences are preselected that will, once assembled, comprise the full-length, ds-DNA. DNA sequence segments, of lengths Lm1, Lm2, Lm3, through Lmn are illustrated in FIG. 1.

The full-length, ds-DNA sequence is a predetermined sequence. Once the specific ds-DNA sequence that is to be synthesized has been determined, the DNA sequence is analyzed by a computer program. There are many very useful computer programs available for analyzing the DNA sequence. The following is a list of available computer programs: USC Computational Biology Software Packages, Department of Molecular Biology, University of Southern California, Los Angeles, Calif. 90089-1113; Array Designer, Primer Premier 5, Xpression Primer's, and NetPrimer by PREMIER Biosoft International, 3786 Corina Way, Palo Alto, Calif. 94303-4504; DoPrimer™ Pro by LION bioscience AG LION bioscience Ltd., Compass House, 80-82 Newmarket Road, Cambridge CB5 8DZ, United Kingdom; GeneFisher, Interactive Primer Design, Institut für Mikrobiologie und Genetik der Georg-August-Universität, Grisebachstrasse 8, 37077 Göttingen, Germany; Cassandra Primers Prediction Software by CBI—the Centre of BioInformatics at Peking University, Peking, China; and Primer Design by Whitehead Institute, Nine Cambridge Center, Cambridge, Mass. 02142-1479.

The multiplicity of shorter ds-DNA sequence segments, of lengths Lm1, Lm2, Lm3, through Lmn, and of predetermined sequences are combined and assembled, as directed by the output of the computer program. The segments are then combined and assembled to produce the desired full length ds-DNA sequence of the desired length, "L."

Figure 2:
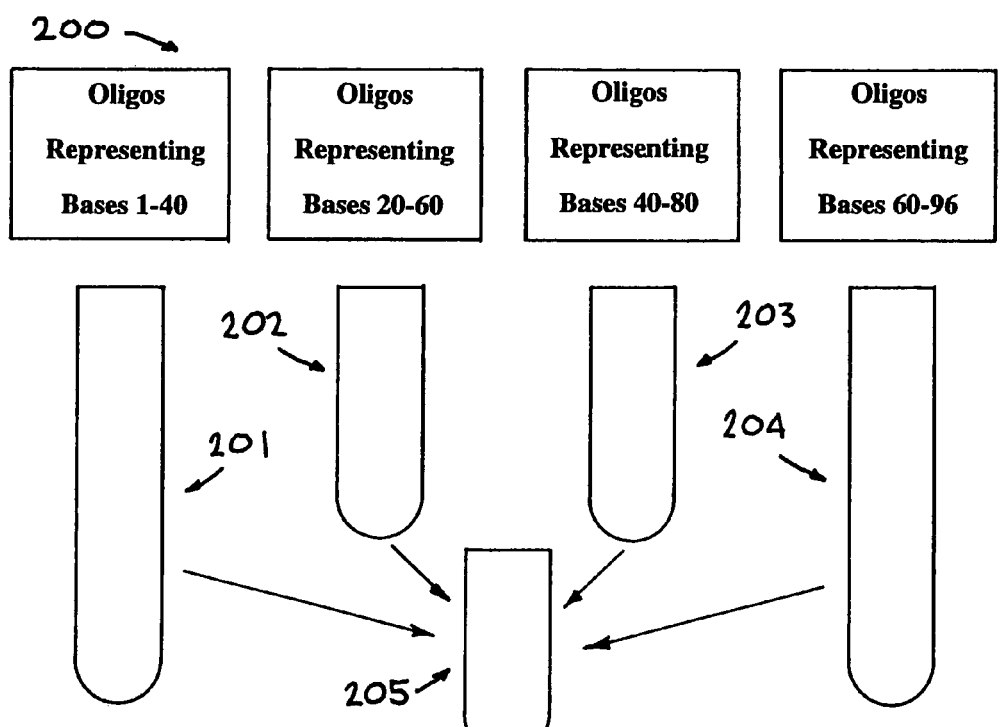
FIG. 2 illustrates the combination and assembly of the multiplicity of shorter ds-DNA sequence segments, of lengths Lm1, Lm2, Lm3, through Lmn, and of predetermined sequences into the desired full length ds-DNA sequence of the desired length, "L."

Referring now to FIG. 2, the system 200 illustrates the combination and assembly of the multiplicity of shorter ds-DNA sequence segments, of lengths Lm1, Lm2, Lm3, through Lmn, and of predetermined sequences into the desired full length ds-DNA sequence of the desired length, "L." The multiplicity of shorter ds-DNA sequence segments, of lengths Lm1, Lm2, Lm3, through Lmn, and of predetermined sequences, previously determined by the output of the computer program, are contained in a multiplicity of storage locations. Oglios representing bases 1-40 are contained in storage location 201. Oglios representing bases 2-60 are contained in storage location 202. Oglios representing bases 40-80 are contained in storage location 203. Oglios representing bases 60-96 are contained in storage location 204. The oglios comprise at least some of the multiplicity of shorter ds-DNA sequence segments, of lengths Lm1, Lm2, Lm3, through Lmn, and of predetermined sequences.

Using either a pipetting robot or voltage-driven fluidic transport, the selected ss-DNA sequence segments are transported to the initial segment of DNA for hybridization of this multiplicity of DNA sequence segments. The multiplicity of DNA sequence segments are ligated to produce the DNA of a desired length and of a predetermined sequence. The process may proceed either by adding and ligating one ss-DNA segment at a time or via the addition and ligation of a multiplicity of ss-DNA segments. The ss-DNA segments that are used to synthesize the ds-DNA segments of length Lm1, Lm2, . . . can be, themselves, synthesized from shorter ss-DNA segments, using non-consumable, tethered templates in a parallel process. Multiple ss-DNA segments may be added, simultaneously, so long as there is only one thermodynamically-favored product. Voltage-driven fluidic transport systems are known in the art. For example, see the article "Active Microelectronic Chip Devices Which Utilize Controlled Electrophoric Fields for Multiplex DNA Hybridization and Other Genomic Applications" by Michael J. Heller, Anita H Foster, and Eugene Tu in Electrophoresis 2000, 21,157-164 (2000). The article "Active Microelectronic Chip Devices Which Utilize Controlled Electrophoric Fields for Multiplex DNA Hybridization and Other Genomic Applications" by Michael J. Heller, Anita H Foster, and Eugene Tu in Electrophoresis 2000, 21,157-164 (2000) is incorporated herein by reference.

Figure 3:
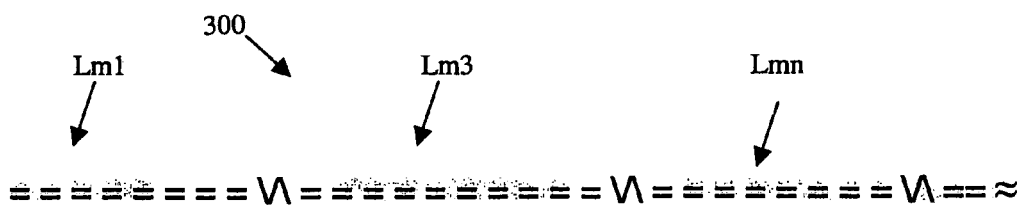
FIG. 3 illustrates a section "gacctgcgca at" (SEQ ID No.: 400>1) of the desired full length ds-DNA sequence.

Referring now to FIG. 3, a section "gacctgcgca at" (SEQ ID No.: 400>1) of the desired full length ds-DNA sequence is illustrated. The section is designated generally by the reference numeral 300. The section 300 is a portion of the desired full length ds-DNA sequence of the desired length, "L." The section 300 contains a multiplicity of shorter ds-DNA sequence segments. As shown, the shorter ds-DNA sequence segments Lm1, Lm3, and Lmn are included. The shorter ds-DNA sequence segments Lm1, Lm3, and Lmn are in the order directed by the output of the computer program.

Figure 4:
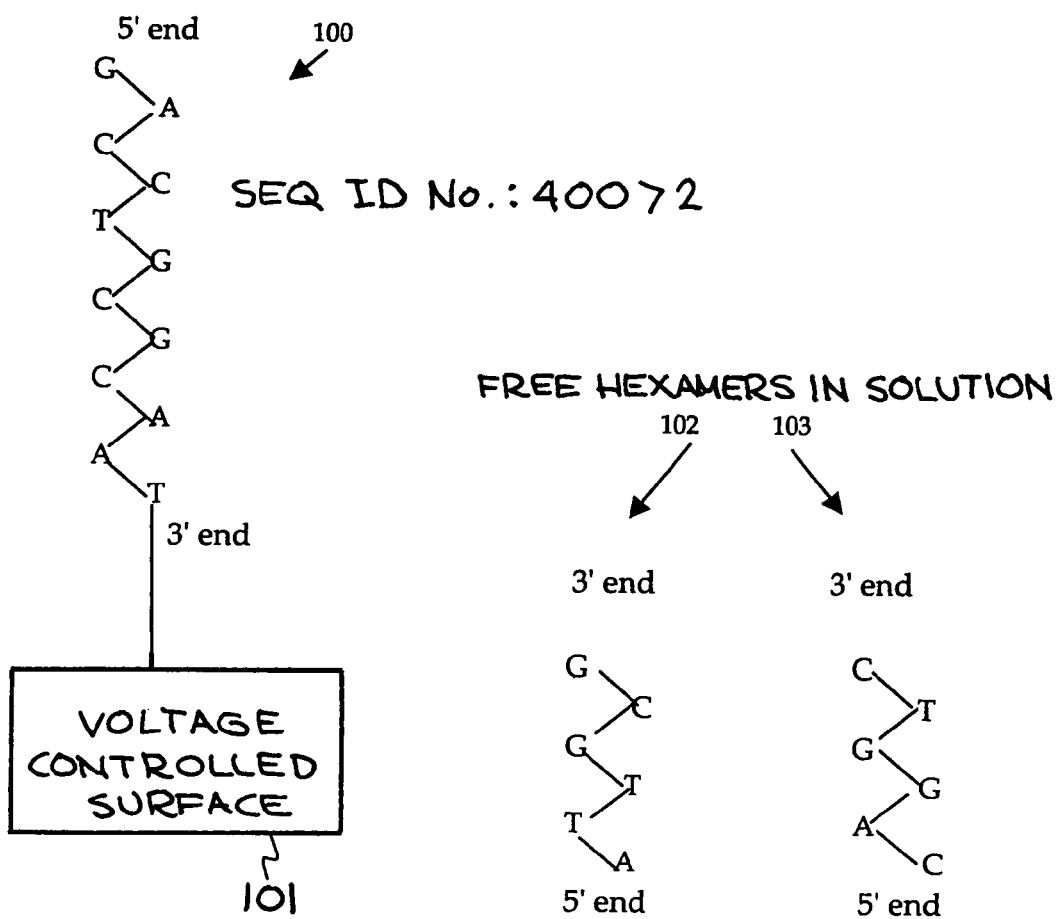
FIG. 4 illustrates a 12-mer "attgcgcagg tc" (SEQ ID No.: 400>2) tethered to a voltage controlled surface.
Figure 5:
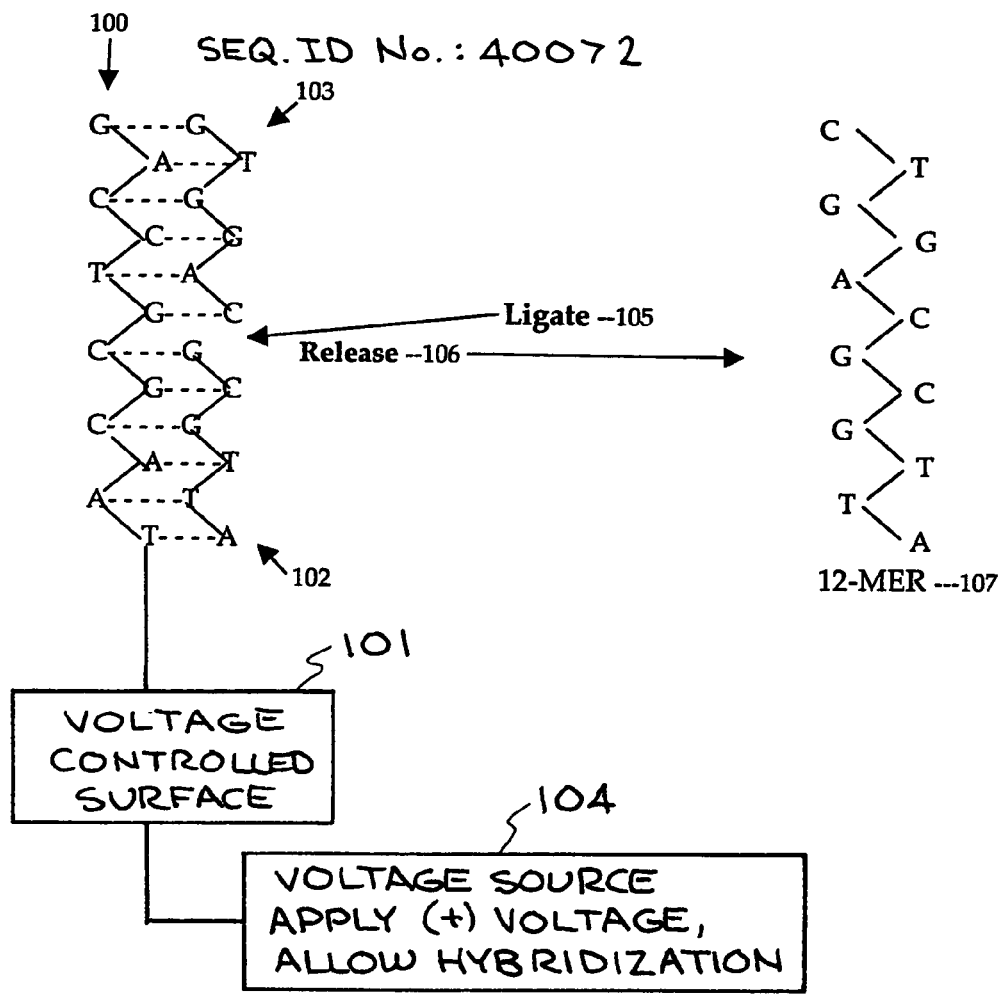
FIG. 5 illustrates a voltage source being utilized to apply a voltage (+) to the voltage controlled surface to allow hybridization.

Referring now to FIGS. 4 and 5, another embodiment of the present invention is illustrated. This embodiment provides a system for synthesizing DNA of lengths up to 10,000 bases and of predetermined sequence. DNA, since it is normally negatively charged in solution, can be effectively transported within a fluidic system using electric fields. This technique can greatly accelerate the process of hybridizing such solution-borne DNA to surface tethered DNA. The system of the present invention combines transport and hybridization with the use of a DNA ligase to synthesize a single strand of length n+m+I (etc.), from two or more separate strands in solution of lengths n, m, I, etc.

For the purposes of illustration, one of the simplest cases is shown in FIGS. 4 and 5, in which there are only two equal-length precursor strands of DNA, each of length "N" bases. The steps utilized are to synthesize and store each of the 4^N N-mers in addressable reservoirs, synthesize and tether every possible 2*N-mer into a spot-addressable array, use field-controlled movement to hybridize the two appropriate N-mers to the desired, tethered 2*N-mer, and ligate the N-mers into the desired 2*N-mer. This avoids the necessity for synthesizing and storing all of the possible 2*N-mers, in advance, as consumables. This permits the overall instrument to utilize a much smaller number of reagent reservoirs and avoids costly and wasteful inclusion of 2*N-oligomers that are not needed. Precursors of any convenient length could be used, so long as the "footprint" of the ligase enzyme couples to the two or more precursor strands, once they have all hybridized to the tethered strand.

The system begins optimally with starting fragments no shorter than 8 bases in length. All 256 possible tetramers are synthesized and stored individually-addressable reservoirs. The tetramers are consumables. An array is provided with all 65,535 octamers, each individually-addressable, electrically.

As illustrated by FIG. 4, a 12-mer "attgcgcagg tc" (SEQ ID No.: 400>2) designated by the reference numeral 100 is tethered to a voltage controlled surface 101. Free hexamers 102 and 103 are in solution. As illustrated by FIG. 5, a voltage source 104 is utilized to apply a voltage (+) to the voltage controlled surface 101 to allow hybridization. The free hexamers 102 and 104 in solution are drawn to 12-mer 100 "attgcgcagg tc" (SEQ ID No.: 400>2). The next step is to ligate into the 12-mer 406. The 12-mer 406 106 is released.

To construct a much longer n-mer, the next 12-mer is synthesized by metering out equal quantities of the needed hexamers, electrophoretically transporting them to the proper location in the array, wait briefly for hybridization, and ligate. The release is electrically-driven and the 12-mer is electrophoretically transported to the growing DNA strand where it is held in position via the magnetic field by its tethering.

The present invention provides different systems for synthesizing a desired double-stranded DNA of a predetermined length and of a predetermined sequence. The systems generally comprise determining preselected sequence segments that will complete the desired double-stranded DNA are determined, providing preselected segment sequences of DNA that will be used to complete the desired double-stranded DNA, and assembling the preselected segment sequences of DNA to produce the desired double-stranded DNA. In one embodiment the determination of the preselected sequence segments that will complete the desired double-stranded DNA comprises analyzing the desired double-stranded DNA by a computer program.

In one embodiment of the present invention the assembling of the preselected segment sequences of DNA to produce the desired double-stranded DNA comprises multiple substeps of assembling individual preselected segment sequences of DNA that complete the desired double-stranded DNA to produce the desired double-stranded DNA. In another embodiment at least some of the multiple substeps are performed in parallel. In another embodiment at least some of the multiple substeps are performed using non-consumable, tethered templates in a parallel process. In another embodiment at least some of the multiple substeps are performed by ligating the individual preselected segment sequences of DNA that complete the desired double-stranded DNA to produce the desired double-stranded DNA. In another embodiment at least some of the multiple substeps are performed using non-consumable, tethered templates in a parallel process. In another embodiment at least some of the multiple substeps themselves comprise assembling subsets of individual preselected segment sequences of DNA and assembling the subsets of preselected segment sequences of DNA to produce the preselected segment sequences of DNA.

It should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of synthesizing a desired double-stranded DNA of a predetermined length and of a predetermined sequence using a computer program, a voltage controlled surface, and a solution, consisting of the steps of:
   using a computer program to analyze the desired double-stranded DNA and determine an initial sequence segment and individual preselected sequence segments that when assembled will complete the desired double-stranded DNA,
   providing said initial sequence segment and
   providing said individual preselected segment sequences of DNA that when assembled will complete the desired double-stranded DNA, and
   assembling said individual preselected segment sequences of DNA to produce the desired double-stranded DNA by multiple substeps of assembling said individual preselected segment sequences of DNA that complete the desired double-stranded DNA to produce the desired double-stranded DNA wherein said multiple substeps include
   tethering said initial individual preselected segment sequences of DNA to the voltage controlled surface,
   applying a voltage to said initial individual preselected segment sequences of DNA,
   placing said individual preselected segment sequences of DNA in the solution,
   drawing said individual preselected segment sequences of DNA in solution to said initial individual preselected segment sequences of DNA, and
   ligating said individual preselected segment sequences of DNA to produce the DNA of a desired length and of a predetermined sequence.

2. The method of synthesizing a desired double-stranded DNA of claim 1 wherein at least some of said multiple substeps are performed in parallel.

3. The method of synthesizing a desired double-stranded DNA of claim 1 wherein at least some of said multiple substeps are performed using non-consumable, tethered templates in a parallel process.

4. The method of synthesizing a desired double-stranded DNA of claim 1 wherein at least some of said multiple substeps comprise sequential substeps of adding and ligating two or more of said individual preselected segment sequences of DNA to produce the desired double-stranded DNA.

5. The method of synthesizing a desired double-stranded DNA of claim 1 wherein at least some of said multiple substeps are performed by the simultaneous addition and ligation of a multiplicity of said individual preselected segment sequences of DNA to produce the desired double-stranded DNA.

6. The method of synthesizing a desired double-stranded DNA of claim 1 wherein at least some of said multiple substeps are performed by in parallel addition and ligation of a multiplicity of said individual preselected segment sequences of DNA to produce said desired double-stranded DNA.

7. The method of synthesizing a desired double-stranded DNA of claim 1 wherein at least some of said multiple substeps are performed by in parallel addition and ligation of a multiplicity of said individual preselected segment sequences of DNA and at least some of said multiple substeps are performed by sequential addition and ligation of a multiplicity of said individual preselected segment sequences of DNA to produce the desired double-stranded DNA.

8. The method of synthesizing a desired double-stranded DNA of claim 1 wherein at least some of said multiple substeps are performed by the addition and ligation of a multiplicity of said individual preselected segment sequences of DNA to produce the desired double-stranded DNA simultaneously in parallel.

9. The method of synthesizing a desired double-stranded DNA of claim 1 wherein at least some of said multiple substeps are performed sequentially, using a process with non-consumable, tethered templates.

10. The method of synthesizing a desired double-stranded DNA of claim 1 wherein at least some of said multiple substeps are performed using a pipetting robot.

11. The method of synthesizing a desired double-stranded DNA of claim 1 wherein at least some of said multiple substeps are performed using a voltage-driven fluidic transport.

12. The method of synthesizing a desired double-stranded DNA of claim 1 wherein at least some of said multiple substeps are performed using a fluidic system containing electric fields.

13. The method of synthesizing a desired double-stranded DNA of claim 1 wherein said step of assembling said individual preselected segment sequences of DNA to produce the desired double-stranded DNA comprises assembling said individual preselected segment sequences of DNA as directed by the output of said computer program.

14. A method of synthesizing DNA of a desired length and of a predetermined sequence using a computer program, a voltage controlled surface, and a solution, consisting of the steps of:
   using the computer program to analyze the desired double-stranded DNA and preselecting an initial segment of the DNA of desired length and of a predetermined sequence,
   using the computer program to analyze the desired double-stranded DNA and preselecting a multiplicity of individual DNA sequence segments that will comprise the DNA of a desired length and of a predetermined sequence,
   assembling said initial segment of DNA and said individual preselected segment sequences of DNA to produce the desired double-stranded DNA by multiple substeps that complete the desired double-stranded DNA, said multiple substeps including
   providing said initial segment of DNA, providing said individual preselected segment sequences of DNA that when assembled will complete the desired double-stranded DNA, tethering said initial segment of DNA to the voltage controlled surface, applying a voltage to said initial segment of the DNA of desired length and of a predetermined sequence by applying a voltage to said voltage controlled surface, placing said individual preselected segment sequences of DNA in the solution, drawing said individual preselected segment sequences of DNA in solution to said initial individual preselected segment sequences of DNA, and ligating said individual preselected DNA sequence segments to produce the DNA of a desired length and of a predetermined sequence.

15. The method of synthesizing DNA of a desired length and of a predetermined sequence of claim 14 wherein said initial segment of DNA is a 12-mer and said multiplicity of DNA sequence segments are 6-mers.

16. The method of synthesizing DNA of a desired length and of a predetermined sequence of claim 14 wherein said step of tethering said initial segment of DNA of said desired length and predetermined sequence comprises tethering to a voltage controlled surface.

17. The method of synthesizing DNA of a desired length and of a predetermined sequence of claim 14 wherein said step of tethering said initial segment of DNA of said desired length and predetermined sequence comprises tethering to a voltage controlled surface and said step of applying a voltage to said initial segment of DNA comprises applying a positive voltage to said voltage controlled surface.

18. The method of synthesizing DNA of a desired length and of a predetermined sequence of claim 14 including the step of electrophoretically transporting said multiplicity of DNA sequence segments that will comprise said DNA of a desired length and of a predetermined sequence to an array.

19. The method of synthesizing DNA of a desired length and of a predetermined sequence of claim 14 including the step of electrophoretically transporting said DNA of a desired length and of a predetermined sequence to a growing DNA strand to form a longer DNA sequence.

20. The method of synthesizing DNA of a desired length and of a predetermined sequence of claim 15 including the steps of metering out equal quantities of additional DNA sequence segments that will comprise said DNA of a desired length and of a predetermined sequence, applying a voltage to said initial segment of DNA of said desired length and predetermined sequence for hybridization of said additional multiplicity of DNA sequence segments, ligating said multiplicity of DNA sequence segments to produce an additional strand of DNA of a desired length and of a predetermined sequence, and electrophoretically transporting said additional strand of DNA of a desired length and of a predetermined sequence to said growing DNA strand to form a longer DNA sequence.

21. A method of synthesizing desired double-stranded long DNA of a predetermined length and of a predetermined sequence using a computer program, a voltage controlled surface, and a solution, consisting of the steps of:

using the computer program to analyze the desired double-stranded DNA and for preselecting an initial segment of DNA of a preselected length and of a predetermined sequence and for preselecting individual segment sequences of DNA to produce the desired double-stranded DNA by multiple substeps of assembling said individual preselected segment sequences, assembling said initial segment of DNA and said individual preselected segment sequences of DNA to produce the desired double-stranded DNA by multiple substeps that complete the desired double-stranded DNA, said multiple substeps including providing said initial segment of DNA, providing said individual preselected segment sequences of DNA that when assembled will complete the desired double-stranded DNA, tethering said initial segment of DNA to the voltage controlled surface, placing said individual preselected segment sequences of DNA in the solution, applying a voltage to said initial segment of DNA by applying a voltage to said voltage controlled surface, drawing said individual preselected segment sequences of DNA in solution to said initial individual preselected segment sequences of DNA, ligating said individual preselected sequence segments to produce the DNA of a desired length and of a predetermined sequence.

* * * * *